(12) United States Patent  (10) Patent No.: US 6,746,478 B2
Jayaraman  (45) Date of Patent: *Jun. 8, 2004

(54) STENT FORMED FROM ENCAPSULATED STENT PREFORMS

(75) Inventor: Swaminathan Jayaraman, Fremont, CA (US)

(73) Assignee: Vascular Concepts Holdings Limited, British Isles (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/286,805

(22) Filed: Nov. 4, 2002

(65) Prior Publication Data

US 2003/0055479 A1 Mar. 20, 2003

Related U.S. Application Data

(63) Continuation of application No. 09/440,926, filed on Nov. 16, 1999, now Pat. No. 6,475,235.

(51) Int. Cl.[7] .................................................. A61F 2/06
(52) U.S. Cl. ...................................................... 623/1.15
(58) Field of Search .............................. 623/1.15, 1.18, 623/1.21, 1.39, 1.42, 1.44, 1.53, 1.54

(56) References Cited

U.S. PATENT DOCUMENTS

| 2,524,661 A | 10/1950 | Harder et al. ................... 75/171 |
| 3,466,166 A | 9/1969 | Levinstein et al. ............... 75/5 |
| 3,562,024 A | 2/1971 | Smith ......................... 148/11.5 |
| 3,657,744 A | 4/1972 | Ersek ................................ 3/1 |
| 4,023,557 A | 5/1977 | Thorne et al. ............... 126/271 |
| 4,281,419 A | 8/1981 | Treace .............................. 3/1.9 |
| 4,300,244 A | 11/1981 | Bokros ............................ 3/1.4 |
| 4,409,172 A | 10/1983 | Ward, Jr. et al. ........... 264/209.2 |
| 4,441,215 A | 4/1984 | Kaster ............................ 3/1.4 |
| 4,465,481 A | 8/1984 | Blake ........................... 604/280 |
| 4,573,242 A | 3/1986 | Lankton et al. ............ 24/16 PB |
| 4,600,446 A | 7/1986 | Torisaka et al. ................. 148/2 |
| 4,640,320 A | 2/1987 | Avison et al. ............... 140/93 A |
| 4,655,771 A | 4/1987 | Wallsten ......................... 623/1 |
| 4,669,474 A | 6/1987 | Barrows ...................... 128/334 |
| 4,718,907 A | 1/1988 | Karwoski et al. ............. 623/12 |
| 4,719,916 A | 1/1988 | Ravo ...................... 128/334 R |
| 4,732,152 A | 3/1988 | Wallsten et al. ............. 128/343 |
| 4,752,054 A | 6/1988 | Jonsson ......................... 248/51 |
| 4,762,128 A | 8/1988 | Rosenbluth ................. 128/343 |
| 4,776,337 A | 10/1988 | Palmaz ....................... 128/343 |
| 4,813,416 A | 3/1989 | Pollak et al. ................ 128/335 |
| 4,816,339 A | 3/1989 | Tu et al. ...................... 428/421 |
| 4,834,755 A * | 5/1989 | Silvestrini et al. ........ 623/13.19 |
| 4,866,816 A | 9/1989 | Caveney ................... 24/16 PB |
| 4,877,030 A | 10/1989 | Beck et al. ................. 128/343 |
| 4,878,906 A | 11/1989 | Lindemann et al. ........... 623/1 |
| 4,879,135 A | 11/1989 | Greco et al. ..................... 427/2 |
| 4,902,290 A | 2/1990 | Fleckenstein et al. .......... 623/1 |
| 4,950,285 A | 8/1990 | Wilk ........................... 606/232 |

(List continued on next page.)

FOREIGN PATENT DOCUMENTS

| EP | 0 395 098 A1 | 4/1990 | |
| EP | 0 659 389 A1 | 10/1993 | |
| WO | WO 96/00103 | 1/1996 | |
| WO | wo 97/40755 | * 11/1997 | ............... 623/2.12 |
| WO | WO 99/32051 | 7/1999 | |

Primary Examiner—David H. Willse
Assistant Examiner—Suzette J. Jackson
(74) Attorney, Agent, or Firm—Fleit Kain Gibbons Gutman Bongini & Bianco; Paul D. Bianco; Martin Fleit

(57) ABSTRACT

The invention relates to a stent for implantation in a body lumen. The stent is formed from stent preforms. Each stent preform includes an elongated metal core, an outer sheath disposed about the core, and caps disposed on the ends of the outer sheath. The outer sheath and caps encapsulate the metal core to prevent the core from directly contacting the body lumen. In an alternative embodiment, an intermediate sleeve is disposed between the core and outer sheath. In another embodiment, a cover or coating may be disposed about the outer sheath.

29 Claims, 2 Drawing Sheets

U.S. PATENT DOCUMENTS

| | | | |
|---|---|---|---|
| 4,986,831 A | 1/1991 | King et al. .................... 623/1 |
| 4,990,158 A | 2/1991 | Kaplan et al. ............. 623/1.15 |
| 5,007,926 A | 4/1991 | Derbyshire ................ 623/1 |
| 5,059,166 A | 10/1991 | Fischell et al. ................ 600/3 |
| 5,059,211 A | 10/1991 | Stack et al. ................. 606/198 |
| 5,064,435 A | 11/1991 | Porter ........................ 623/12 |
| 5,078,726 A | 1/1992 | Kreamer .................... 606/194 |
| 5,078,736 A | 1/1992 | Behl ............................. 623/1 |
| 5,084,065 A | 1/1992 | Weldon et al. ................. 623/1 |
| 5,100,429 A | 3/1992 | Sinofsky et al. ............ 606/195 |
| 5,104,403 A | 4/1992 | Brotzu et al. .................. 623/1 |
| 5,116,360 A | 5/1992 | Pinchuk et al. ................ 623/1 |
| 5,123,917 A | 6/1992 | Lee ............................... 623/1 |
| 5,147,385 A | 9/1992 | Beck et al. .................... 623/1 |
| 5,147,400 A * | 9/1992 | Kaplan et al. ............ 623/13.18 |
| 5,156,620 A | 10/1992 | Pigott ............................ 623/1 |
| 5,156,623 A | 10/1992 | Hakamatsuka et al. ....... 623/11 |
| 5,158,548 A | 10/1992 | Lau et al. ..................... 604/96 |
| 5,163,951 A | 11/1992 | Pinchuk et al. ................ 623/1 |
| 5,180,366 A | 1/1993 | Woods ........................ 604/96 |
| 5,192,307 A | 3/1993 | Wall .............................. 623/1 |
| 5,192,310 A | 3/1993 | Herweck et al. ............... 623/1 |
| 5,192,311 A | 3/1993 | King et al. .................... 623/1 |
| 5,195,984 A | 3/1993 | Schatz ........................ 606/195 |
| 5,197,977 A | 3/1993 | Hoffman, Jr. et al. .......... 623/1 |
| 5,217,026 A | 6/1993 | Stoy et al. ................... 128/772 |
| 5,234,456 A | 8/1993 | Silvestrini .................... 606/194 |
| 5,234,457 A | 8/1993 | Andersen ..................... 606/198 |
| 5,258,020 A | 11/1993 | Froix ............................. 623/1 |
| 5,279,594 A | 1/1994 | Jackson ....................... 604/265 |
| 5,282,823 A | 2/1994 | Schwartz et al. ........... 606/198 |
| 5,282,824 A | 2/1994 | Gianturco ................... 606/198 |
| 5,289,831 A | 3/1994 | Bosley ........................ 128/899 |
| 5,290,271 A | 3/1994 | Jernberg ................. 604/891.1 |
| 5,304,220 A | 4/1994 | Maginot ........................ 623/1 |
| 5,306,286 A | 4/1994 | Stack et al. ................. 606/198 |
| 5,330,500 A | 7/1994 | Song .......................... 606/198 |
| 5,366,504 A | 11/1994 | Andersen et al. ............. 623/11 |
| 5,383,926 A | 1/1995 | Lock et al. .................... 623/1 |
| 5,387,235 A | 2/1995 | Chuter ........................... 623/1 |
| 5,389,106 A | 2/1995 | Tower ......................... 606/198 |
| 5,456,713 A | 10/1995 | Chuter ........................... 623/1 |
| 5,507,771 A | 4/1996 | Gianturco ................... 606/198 |
| 5,522,881 A | 6/1996 | Lentz ............................. 623/1 |
| 5,556,414 A | 9/1996 | Turi ............................ 606/198 |
| 5,628,787 A * | 5/1997 | Mayer ....................... 623/1.15 |
| 5,630,840 A | 5/1997 | Mayer ........................... 623/1 |
| 5,632,840 A | 5/1997 | Campbell .................... 156/196 |
| 5,649,977 A | 7/1997 | Campbell ....................... 623/1 |
| 5,674,241 A | 10/1997 | Bley et al. ................... 606/198 |
| 5,679,470 A | 10/1997 | Mayer ......................... 428/662 |
| 5,700,286 A | 12/1997 | Tartaglia et al. ............... 623/1 |
| 5,725,570 A | 3/1998 | Heath ........................ 623/1.15 |
| 5,766,204 A | 6/1998 | Porter et al. ................ 606/198 |
| 5,800,511 A | 9/1998 | Mayer ........................... 623/1 |
| 5,824,046 A | 10/1998 | Smith et al. ................... 623/1 |
| 5,824,077 A | 10/1998 | Mayer .......................... 623/11 |
| 5,836,962 A | 11/1998 | Gianotti ..................... 606/191 |
| 5,843,166 A | 12/1998 | Lentz et al. .................... 623/1 |
| 5,855,600 A | 1/1999 | Alt ................................. 623/1 |
| 5,858,556 A | 1/1999 | Eckert et al. ................ 428/586 |
| 5,910,168 A | 6/1999 | Myers et al. ............... 623/1.15 |
| 5,957,974 A * | 9/1999 | Thompson et al. ........ 623/1.13 |
| 5,980,564 A | 11/1999 | Stinson ..................... 623/1.38 |
| 6,099,559 A | 8/2000 | Nolting ...................... 623/1.16 |
| 6,162,537 A | 12/2000 | Martin et al. ............... 428/373 |
| 6,187,039 B1 | 2/2001 | Hiles et al. ................ 623/1.44 |
| 6,214,040 B1 | 4/2001 | Jayaraman ................. 623/1.13 |
| 6,241,691 B1 * | 6/2001 | Ferrera et al. ............. 600/585 |
| 6,342,068 B1 | 1/2002 | Thompson ................. 623/1.53 |
| 6,475,235 B1 * | 11/2002 | Jayaraman ................. 623/1.15 |
| 6,494,907 B1 * | 12/2002 | Bulver ....................... 623/1.22 |

\* cited by examiner

STENT FORMED FROM ENCAPSULATED STENT PREFORMS

This is a continuation of application Ser. No. 09/440,926, filed Nov. 16, 1999 now U.S. Pat. No. 6,475,235.

FIELD OF THE INVENTION

The invention relates to a device for supporting a body lumen. More particularly, the invention is related to a stent formed from stent preforms. Each stent preform has a core that is completely isolated from the lumen walls for supporting a body lumen.

BACKGROUND OF THE INVENTION

The importance of stents in modern medical treatments cannot be over-emphasized. Stents have revolutionized the care of patients by allowing far less invasive and risky surgical procedures to be undertaken. In coronary care, for example, complications following angioplasty can result in acute damage to artery walls, which prior to the development of stent technology required immediate bypass surgery. Stents are now recognized as a viable means of avoiding such procedures, because implantation of such a mechanical device into the area of concern allows the artery walls to be reinforced with permanent artificial scaffolding. Additionally, stents are now recognized as an effective modality for reducing the frequency of restenosis, the recurrent narrowing of the lumen (cavity or channel within a body tube).

Balloon treatment of narrowed arteries can initially increase the diameter of the artery by compressing blockage. However, recoil may result in lumen of insufficient diameter. Such recoil can be hindered by using a stent to dictate the diameter that the lumen is to assume.

Stent delivery and deployment may be performed by balloon mounting the stent and using a catheter to access the area of concern. By inflating the balloon at the lumen defect site, the stent may be expanded to the optimal size to support the lumen. Multiple stents may be deployed as necessary to accommodate defects of larger size or multiple defect locations.

Through the use of stent delivery systems, successful implantations can result in remarkable increase in blood flow, and over time new tissue growth in the area of the implant allows the lumen to maintain a typical structure.

It should be no surprise, however, that as a foreign object introduced into the body, the stent implant may also produce undesirable results. Among the problems encountered with implantation are tearing or cracking of the artery lining. In addition, the stent may irritate the lumen, resulting in blood clot formation on the stent itself. Serious consequences may result, including the need for further invasive procedures and concomitant increased risks.

Thus, there is a need for improved stents which minimize damage to the lumen as a result of interaction of the stent with the lumen, thereby allowing the management of acute vessel dissection and occlusion, decreasing the rate of restenosis, and increasing the safety and efficacy of stent treatments. There is also a need to reduce the frequency of stent thrombosis, the formation of solid masses from blood constituents caused by the thrombogenic surface of prior art stents, by providing a stent preform that when formed as a stent is less likely to damage the lumen.

Stents designed for use in arteries are currently fabricated in metal wireform or tubular shapes that are laser cut. Wireforms may be twisted or coiled mechanically using manual or automatic coil winding machines, or otherwise braided or knitted with similarly useful technology. Individual or multiple stent preforms may be used to create the stent. Prior art stents include metal-polymer composites, in which a metal layer is sandwiched between two layers of a polymer. Alternatively, the faces of the metal layer are coated using thin film deposition techniques, such as Pulsed Laser Deposition, which allow polymer films of micron-level thickness to be applied. The metal layer may also be sandwiched between two layers of biologic material.

The in vivo expansion of the stent using a balloon or other expansion device can create mechanical trauma at the site of application. When using a balloon, for example, the surface of the stent impacts the wall of the artery with a force equivalent to the pressurization of the balloon, and the trauma to the vessel wall from this impact can lead to undesirable tissue proliferation in the long-term. In almost one-quarter of all stent implantations, restenosis through tissue ingrowth occurs. The polymer-overlayer stents with exposed core ends cause inflamation and thrombosis. Furthermore, during the pulsatile force inside the artery, the stent continuously rubs against the artery wall, creating trauma in the region of the implant and to soft tissues of the vessel wall.

In this regard, the present invention is directed to a stent preform that isolates the core of the stent from the body lumen to prevent undesirable additional trauma in the lumen.

SUMMARY OF THE INVENTION

The present invention relates to a stent preform for implantation in a body lumen. The stent preform includes an elongated metal core having first and second core ends, a contact surface, and a solid cross-section, and a hollow outer sheath made of a biocompatible polymer and having first and second sheath ends, caps disposed on the sheath ends, and an interior surface. The outer sheath surrounds and contacts the contact surface of the core to prevent the core from directly contacting the body lumen.

The stent preform may include an elongated core that is expandable, and the outer sleeve may be capable of deforming to compensate for dimensional changes in the cross-section of the expanded core. The cross-section of the core of the stent preform may be substantially cylindrical.

The biocompatible polymer of the outer sheath may be formed of a heat-shrinkable polymer material. The outer sheath also may be formed from a polymer tape.

Preferably, the stent preform may include an elongated core that is formed of a shape-memory alloy. The outer sheath may be made of a polymer film having a thickness between about 0.1 micron and about 5 millimeters. In a preferred embodiment, the sheath caps of the stent preform have a generally rounded contour to minimize stress concentration along the walls of the lumen. The stent preform may also include a cover of a biological or synthetic coating to minimize interference of the stent preform with normal blood function. The coating may be an anticoagulent selected from the group of heparin, hirudin, coumadin, tichlopidiene, and chlopidogrel. The coating may also be disposed in micropores in the outer sheath, allowing controlled release of constituents of the coating.

In another embodiment, the stent preform includes an elongated metal core having first and second core ends, a contact surface, and a solid cross-section, at least one intermediate sleeve disposed between the outer sheath and the core, and a hollow outer sheath made of a biocompatible polymer and having first and second sheath ends, caps disposed on the sheath ends, and an interior surface. The outer sheath surrounds the intermediate sleeve and contact surface of the core to prevent the sleeve and core from directly contacting the body lumen.

The at least one intermediate sleeve may be a lubricious lining, with the core and the lining forming a composite body that is configured and dimensioned to be slidably received by the outer sheath. In a preferred embodiment, the outer sheath and the lining may form a composite body that is configured and dimensioned to be slidably received by the core.

In another embodiment, a filamentary member for implantation in a body lumen includes a rigid inner filament with first and second filament ends, and an outer sheath with first and second sheath ends. Preferably, the outer sheath is made of a biocompatible polymer, and the outer sheath completely encapsulates the inner filament to prevent the core from directly contacting a wall of a body lumen. The inner filament may be made of a plurality of woven fibers. The inner filament may be made from carbon fiber, kevlar, or glass fiber.

The present invention also relates to a method of making a stent preform. The method includes the steps of: providing an elongated core; completely surrounding the core with a polymer jacket to create a composite; heat treating the composite to promote bonding of the core and jacket; and bending the composite to a desired shape.

Preferably, the elongated core is made of metal. The metal may be a shape-memory alloy, and the polymer jacket may be formed of a biocompatible polymer.

In a preferred embodiment, the elongated core is expandable, and the polymer jacket is capable of deforming to compensate for dimensional changes in the cross-section of the expanded core.

The method may also include the step of heat treating the elongated core prior to encapsulating the core with a polymer jacket.

In a preferred embodiment, the polymer jacket is formed of a tape of a biocompatible polymer.

In another embodiment, a method of making a stent preform includes the steps of: providing an elongated metal core; completely encapsulating the core with a polymer tape to create a composite; and bending the composite to a desired shape. The tape may be a vascular fabric.

In another embodiment, a method of making a stent preform comprising the steps of: providing an elongated core made of a shape-memory material; completely encapsulating the core with a biocompatible fabric to create a composite; and bending the composite to a desired shape. At least one intermediate sleeve may be disposed between the biocompatible fabric and the core.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENT

Figure 1:
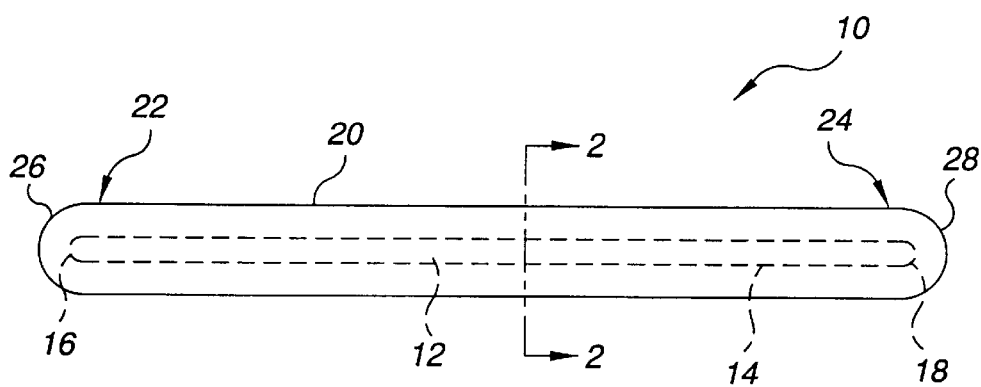
FIG. 1 shows a schematic representation of the overall system of the present invention.

FIG. 1 shows a first embodiment of the stent preform 10 of the present invention. Stent preform 10 includes core 12 with contact surface 14 and core ends 16, 18. The core 12 is preferably made of a rigid or rigidizable material. It may additionally be formed of a material that exhibits suitable ductility, with the material further being chosen based on its radiopacity in order to allow x-ray imaging. Various metals are appropriate for the substrate core, including but not limited to stainless steel, titanium, nickel, and combinations and alloys thereof. In particular, alloys that display the "shape memory" effect, such as a Ni-50% Ti alloy and several copper-base alloys, are appropriate. In a preferred embodiment, Nitinol is used for core 12. As known to those skilled in the art, proper heat treatment of shape memory alloys allows structures to be created which assume several configurations depending on the temperature. Thus, a first shape can be used to facilitate implantation of the stent, and warming of the stent in the body lumen permits the stent to transform to a second shape that provides mechanical support to an artery. The second shape may be in the form of a coil to embolize a part of the anatomy or close a duct, or a mechanical scaffolding structure for vascular or nonvascular purposes. Also, cobalt-based alloys such as Eligiloy may be used as a metal core.

Other stiff materials can also be used to form core 12, including carbon fibers, Kevlar, glass fibers, or the like. Some fiber filaments may not retain enough memory to maintain a preselected stent or coil shape. Thus, the stent may be fabricated by braiding several such filaments together to form a tubular structure. The filaments may be stretched to create a low profile, while releasing the filament from a stretched state allows it to assume a desirable shape. As is known to those skilled in the art, various braiding techniques may be employed, as well as various polymers or fillers. The core is preferably substantially cylindrical in shape, although other core cross-sections may be used such as rectangular or hexagonal configurations.

As further seen in FIG. 1, core 12 is surrounded by outer sheath 20 having sheath ends 22, 24 and caps 26, 28. Sheath 20 serves as a sleeve or jacket which surrounds core 12 to prevent the core from directly contacting a wall of a body lumen. Sheath 20 is preferably thin, and preferably an ultra thin tube of extruded polymer which may be microporous or macroporous. Although the sheath 20 may even have a thickness on the submicron level, in a preferred embodiment the sheath 20 has a thickness of between about 0.1 microns and 5 millimeters. The outer sheath 20 may be heat treated to ensure adhesion or bonding of the sheath to the core. It may also be necessary to heat the composite to melt the polymer and permit it to flow, thereby not only allowing more effective bonding with the core but also filling any gaps that may exist that expose the core.

Figure 2:
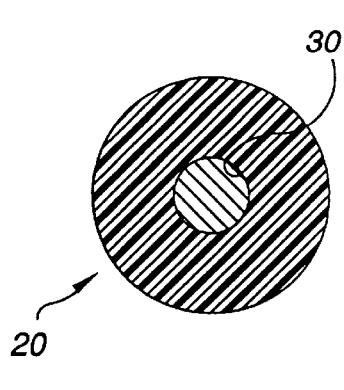
FIG. 2 shows a transverse cross-sectional view through a first embodiment of the stent preform.

Suitable polymers for this application include biocompatible polymers of particular permeability. The polymers can form a permeable, semi-permeable, or non-permeable membrane, and this property of the polymer may be selected during or after extrusion depending upon the particular polymer chosen. As shown in FIG. 2, sheath 20 has an interior surface 30, which closely communicates with the contact surface 14 of the core 12. Numerous polymers are appropriate for use in stent preform 10, including but not limited to the polymers PTFE, ePTFE, PET, polyamide, PVC, PU, Nylon, hydrogels, silicone, silk, knitted or woven polyester fabric, or other thermosets or thermoplastics. In a preferred embodiment, the polymer is selected as a heat-shrinkable polymer. The sheath may also be in the form of a thin film, which is deposited over the entire surface of core 12. A layer or multiple layers of submicron particles (nanoparticles) may also create a nanotube surrounding core 12. Sheath 20 must completely encapsulate core 12, and thus areas of the sheath form end caps 26, 28.

Outer sheath 20 may be knitted or woven to form a braided configuration, however a sheath formed in this manner must still completely encapsulate core 20. Sufficient tightness of the braiding around the core is required, or alternatively the strands may be sealed together to form a continuous surface after braiding. The braided configuration is also designed to cover the ends 16, 18 of core 12.

Figure 3:
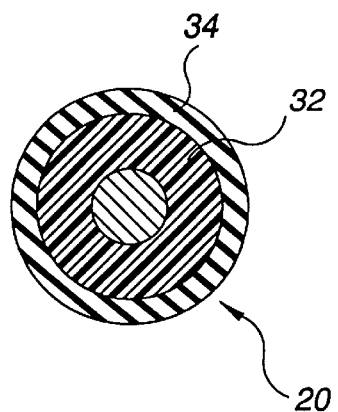
FIG. 3 shows a transverse cross-sectional view through a second embodiment of the stent preform.

FIG. 3 shows an outer sheath 20 formed of several layers of material. The layers may be of the same or varying thickness, and may be the same or different materials. In a preferred embodiment, layer 32 is formed of a first polymer, and layer 34 is a biological or other synthetic coating which can preserve blood function. However, the biological material must be able to completely encapsulate the core 12, even after the core has been coiled or braided and formed into the shape of a stent. Thus, the biological coating should resist tearing and delamination which could result in exposure of core 12. If such a coating is applied prior to shaping the preform into a stent, it should be capable of withstanding the deformations and stresses that are induced by coil winding or braiding machines. It should also be capable of withstanding elevated temperatures if heat treatments are necessary.

The coating may be an anticoagulent material such as heparin, coumadin, tichlopidiene, and chlopidogrel. The coating may also be a genetic material such as angiogenic factors, tissue inhibiting material, growth factors such as VEGF, PDGF, and PGF, as well as thrombin inhibiting factors. The growth factors and angiogenic factors can be sourced biologically, for example through porcine, bovine, or recombinant means, and the growth factors even can be derived from the patient's own body by processing blood from the patient. The coating may be applied to the polymer layer by dipping the outer sheath into growth factors for several minutes to promote attachment, and additional factors may be added to help effectuate the attachment. The growth factors can further be encapsulated in a release mechanism made of liposomes, PLA, PGA, HA, or other release polymers. Alternatively, the growth factors can be encapsulated in non-controlled release, naturally-derived polymers such as chitosan and alginate.

In an alternate embodiment, the coating can be sandwiched between the micropores of the polymer layer so that a controlled release occurs. In yet another alternate embodiment, a multilayer outer sheath 20 can be formed wherein an active release substrate polymer is attached to a layer of a different polymer, or sandwiched between two layers of either the same or different polymers. Outer sheath 20 may otherwise be formed of an inert polymer, or of an inert polymer surrounding an active polymer.

Figure 4:
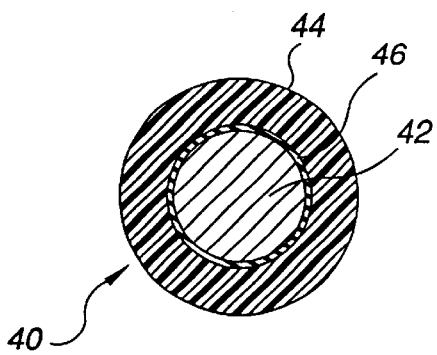
FIG. 4 shows a third embodiment of the stent preform including a lubricious lining.
Figure 5:
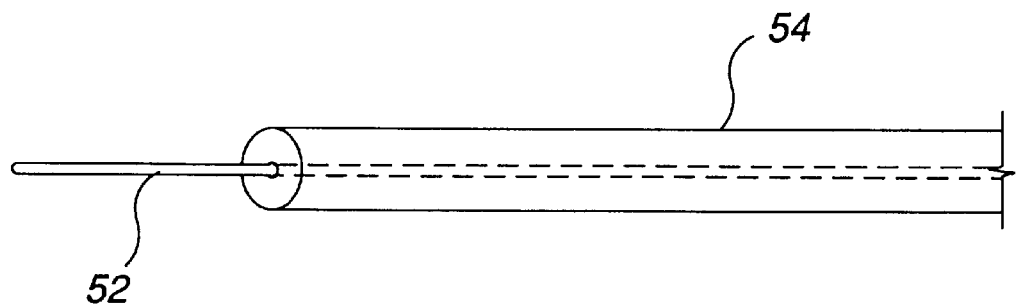
FIG. 5 shows a fabrication scheme for the stent preform.

FIG. 4 shows another embodiment of a stent preform 40 according to the present invention. Stent Preform 40 includes core 42 and outer sheath 44. A lubricious lining 46 is disposed between core 42 and outer sheath 44 to facilitate insertion of core 42 into the sheath. The lubricious lining 46 may be attached to core 42 or outer sheath 44, or it may be separate. The lining permits a tight fit between core 42 and outer sheath 44 by providing a lubricated surface on which either can be slid relative to the other, thereby allowing the inner dimension of the outer sheath to very closely match the outer dimension of the core. FIG. 5 shows a core 52 being inserted into an outer sheath 54.

Figure 6:
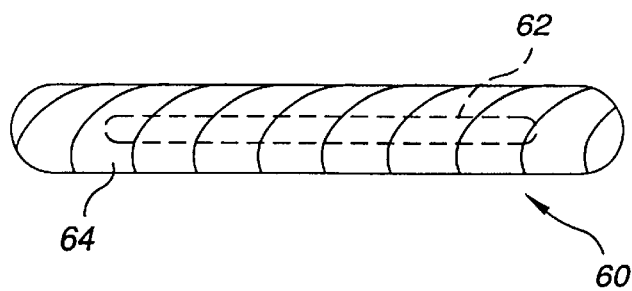
FIG. 6 shows a fourth embodiment of the stent preform using a tape outer sheathing.

FIG. 6 shows a stent preform 60 with core 62 (shown in cutaway) wrapped in a tape 64. The tape 64 completely covers core 62 so that the core is isolated from the lumen walls after implantation. In an alternate embodiment, the tape is applied around a core that is already covered with another coating or layer of polymer. The tape may be applied to the core using a winding machine or other suitable means.

The tape is preferably a thin polymer. Various polymers can be produced in tape form, for example teflon tape that may have a thickness of between 0.01 millimeters and 2 millimeters, and preferably less than 0.1 millimeter. Such a tape advantageously may be self-lubricating. The tapes may be used in the form of foils with metallic or polymer films, and may be coated with adhesive backings. The tapes may furthermore be produced of biocompatible fabrics, including vascular grafts and fabrics.

Figure 7:
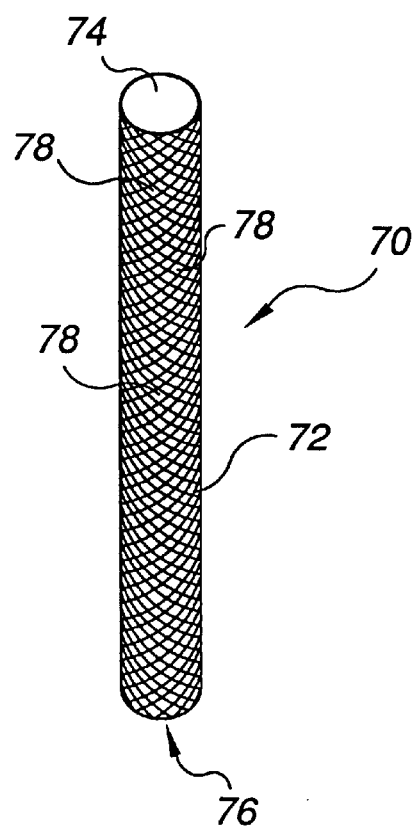
FIG. 7 shows another embodiment of the stent preform in a braided configuration.

FIG. 7 shows a braided stent 70 made from stent preform 72. In an alternative embodiment of braided stent 70, multiple stent preforms may be used. Ends 74 and 76 may be pulled to extend the braided stent to a longer length, thereby also decreasing the inner diameter of the stent. When released, the braided stent returns to a relaxed length and diameter. Open areas 78 between the preform walls permit new tissue growth which may eventually cover the stent structure. The braided stent, or other shapes or coils forming a stent, can be mounted on top of an expansile device such as a balloon catheter, which expands the stent from a relaxed diameter to an elongated diameter.

A delivery housing in combination with a shaft may be used to insert the stent into a lumen. The housing may have a cylindrical shape, and the stent, loaded on the shaft in extended state, is placed in the housing. Once the housing is inserted into the lumen, the stent may be slowly withdrawn from the housing while supported and guided by the shaft, and allowed to return to its unextended shape having a greater diameter. The housing and shaft are completely withdrawn from the lumen leaving the stent as a lining inside the vessel wall to exclude blockage from the vessel. By emobilizing the duct with a stent having an isolated core, the stent is more readily accepted by the body. This implantation method can be applied to any anatomical conduit.

Stents incorporating shape memory materials may be heat treated in various states to permit the stretched configuration. Although the core may require treatment at 650° C., care must be exercised when fabricating the stents of the present invention since a polymer overlayer will be provided.

Stent preforms may be spooled to permit storage in a roll form, or may also be kept in an unrolled state.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A stent for implantation in a body lumen comprising a plurality of stent preforms, wherein at least one stent preform includes an elongated metallic core, an outer sheath disposed about the core, and caps disposed on the ends of the outer sheath thereby encapsulating the core.

2. A stent as defined in claim 1 wherein the stent preforms are braided to form a tubular structure.

3. A stent as defined in claim 2 wherein at least one stent preform includes a cover disposed about the outer sheath, the cover being a biological or synthetic material to minimize interference of the stent preform with normal blood function.

4. A stent as defined in claim 3 wherein the cover is made of an anticoagulant selected from the group of heparin, hirudin, coumadin, tichlopidiene, and chlopidogrel.

5. A stent as defined in claim 2 wherein the elongated metallic core is expandable, and the outer sleeve is capable of deforming to compensate for dimensional changes of the expandable core.

6. A stent as defined in claim 5 wherein the metallic core is formed of a shape-memory alloy.

7. A stent as defined in claim 5 wherein the outer sheath is formed of a heat-shrinkable polymer material.

8. A stent as defined in claim 5 wherein the outer sheath is formed of a polymer tape.

9. A stent as defined in claim 5 wherein the outer sheath is formed of a biocompatible fabric.

10. A stent for implantation in a body lumen comprising a plurality of stent preforms, wherein at least one stent preform includes an elongated metallic core, an intermediate sleeve disposed about the core, an outer sheath disposed about the intermediate sleeve, and caps disposed on the ends of the outer sheath thereby encapsulating the intermediate sleeve and core.

11. A stent as defined in claim 10 wherein the stent preforms are braided to form a tubular structure.

12. A stent as defined in claim 11 wherein at least one intermediate sleeve is a lubricious lining thereby allowing the intermediate sleeve to be slidably received by the elongated metallic core.

13. A stent as defined in claim 11 wherein at least one intermediate sleeve is a lubricious lining thereby allowing the outer sheath to be slidably received by the intermediate sleeve.

14. A stent as defined in claim 11 wherein at least one stent preform includes a biocompatible coating disposed on the outer sheath and caps.

15. A stent as defined in claim 14 wherein the biocompatible coating includes growth enhancers.

16. A stent as defined in claim 15 wherein the growth enhancers are encapsulated in a release mechanism.

17. A stent for implantation in a body lumen comprising a plurality of stent preforms, wherein at least one stent preform includes an elongated inner filament, an outer sheath disposed about the inner filament, and caps disposed on the ends of the outer sheath thereby encapsulating the inner filament.

18. A stent as defined in claim 17 wherein the stent preforms are braided to form a tubular structure.

19. A stent as defined in claim 18 wherein at least one stent preform includes a cover disposed about the outer sheath, the cover being a biological or synthetic material to minimize interference of the stent perform with normal blood function.

20. A stent as defined in claim 19 wherein the cover is made of an anticoagulant selected from the group of heparin, hirudin, coumadin, tichlopidiene, and chlopidogrel.

21. A stent as defined in claim 18 wherein the elongated inner filament is expandable, and the outer sleeve is capable of deforming to compensate for dimensional changes of the expandable inner filament.

22. A stent as defined in claim 21 wherein the inner filament is formed of a plurality of woven fibers.

23. A stent as defined in claim 21 wherein the outer sheath is formed of a heat-shrinkable polymer material.

24. A stent as defined in claim 21 wherein the outer sheath is formed of a polymer tape.

25. A stent as defined in claim 21 wherein the outer sheath is formed of a biocompatible fabric.

26. A stent for implantation in a body lumen comprising a plurality of stent preforms, wherein at least one stent preform includes an elongated inner filament, an intermediate sleeve disposed about the inner filament, an outer sheath disposed about the intermediate sleeve, and caps disposed on the ends of the outer sheath thereby encapsulating the intermediate sheath and inner filament.

27. A stent as defined in claim 26 wherein the stent preforms are braided to form a tubular structure.

28. A stent as defined in claim 27 wherein at least one intermediate sleeve is a lubricious lining thereby allowing the intermediate sleeve to be slidably received by the elongated inner filament.

29. A stent as defined in claim 27 wherein at least one intermediate sleeve is a lubricious lining thereby allowing the outer sheath to be slidably received by the intermediate sleeve.

* * * * *